(12) United States Patent
Li et al.

(10) Patent No.: US 8,173,643 B2
(45) Date of Patent: May 8, 2012

(54) N-SUBSTITUTED THIOMORPHOLINE DERIVATIVES AS THE INHIBITORS OF DIPEPTIDYL PEPTIDASE IV AND THE PHARMACEUTICAL USES THEREOF

(75) Inventors: Song Li, Beijing (CN); Wu Zhong, Beijing (CN); Junhai Xiao, Beijing (CN); Xinghai Ma, Beijing (CN); Lili Wang, Beijing (CN); Hongying Liu, Beijing (CN); Zhibing Zheng, Beijing (CN)

(73) Assignee: Beijing Molecule Science and Technology Co., Ltd., Beijing (CN)

( * ) Notice: Subject to any disclaimer, the term of this patent is extended or adjusted under 35 U.S.C. 154(b) by 316 days.

(21) Appl. No.: 12/593,717

(22) PCT Filed: Jun. 1, 2007

(86) PCT No.: PCT/CN2007/001757
§ 371 (c)(1),
(2), (4) Date: Sep. 29, 2009

(87) PCT Pub. No.: WO2008/119208
PCT Pub. Date: Oct. 9, 2008

(65) Prior Publication Data
US 2010/0113433 A1 May 6, 2010

(30) Foreign Application Priority Data

Apr. 3, 2007 (CN) .......................... 2007 1 0090694

(51) Int. Cl.
*C07D 295/185* (2006.01)
*A61K 31/54* (2006.01)
(52) U.S. Cl. ...................... 514/227.5; 544/59
(58) Field of Classification Search .................... 544/59; 514/227.5
See application file for complete search history.

(56) References Cited

U.S. PATENT DOCUMENTS

| 5,538,950 | A | 7/1996 | Hemmi et al. |
| 6,107,329 | A * | 8/2000 | Hoover et al. ............... 514/415 |
| 6,277,877 | B1 | 8/2001 | Hoover et al. |
| 6,949,515 | B2 | 9/2005 | Demuth et al. |
| 2005/0043299 | A1 | 2/2005 | Evans et al. |
| 2005/0070719 | A1 | 3/2005 | Belyakov et al. |
| 2005/0209159 | A1 | 9/2005 | Demuth et al. |
| 2008/0255126 | A1 | 10/2008 | Evans et al. |
| 2008/0312236 | A1 | 12/2008 | Leblond et al. |
| 2009/0036436 | A1 | 2/2009 | Leblond et al. |
| 2009/0088433 | A1 | 4/2009 | Leblond et al. |
| 2009/0318499 | A1 | 12/2009 | Leblond et al. |

FOREIGN PATENT DOCUMENTS

WO   WO 9639384 A1 * 12/1996

OTHER PUBLICATIONS

Supplementary European Search Report, Application No. EP 07 72 1330, dated Dec. 15, 2010.
Karasawa et al., "Preparation of Quinazoline Derivatives for Treatment of Digestive Diseases," XP002614302, Database CA [Online], Chemical Abstracts Service, dated Oct. 7, 1999.

* cited by examiner

*Primary Examiner* — Kahsay T Habte
(74) *Attorney, Agent, or Firm* — MacMillan, Sobanski & Todd, LLC

(57) ABSTRACT

The present invention relates to N-Substituted thiomorpholine compounds of formula I, the possible isomers, the pharmaceutically acceptable salts, the solvates, the hydrates or the prodrugs thereof as inhibitors of dipeptidyl peptidase IV (DPP-IV); and to a method for preparing the compounds of formula I, pharmaceutical compositions comprising the compounds of formula I and use of the compounds of formula II in medical field, particularly in the preparation of medicaments for treating and preventing diabetes (in particular type II diabetes), hyperglycemia, X syndrome, hyperinsulinemia, obesity, atherosclerosis and all kinds of diseases modulated by immune system.

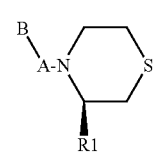

10 Claims, No Drawings

N-SUBSTITUTED THIOMORPHOLINE DERIVATIVES AS THE INHIBITORS OF DIPEPTIDYL PEPTIDASE IV AND THE PHARMACEUTICAL USES THEREOF

CROSS REFERENCE TO RELATED APPLICATION

This application is the National Phase of International Application PCT/CN2007/001757 filed Jun. 1, 2007 which designated the U.S., and that International Application was published in Chinese under PCT Article 21(2) on Oct. 9, 2008 as International Publication Number WO 2008/119208 A1. PCT/CN2007/001757 claims priority to Chinese Application No. 200710090694.2, filed Apr. 3, 2007. Thus, the subject nonprovisional application claims priority to Chinese Application No. 200710090694.2, filed Apr. 3, 2007. The disclosures of both applications are incorporated herein by reference.

TECHNICAL FIELD

The present invention relates to N-substituted thiomorpholine derivatives, or the possible isomers, the pharmaceutically acceptable salts, the hydrates or the prodrugs thereof as inhibitors of dipeptidyl peptidase IV (DPP-IV), and to a method for preparing the compounds of formula I, pharmaceutical compositions comprising the compounds of formula I, and use of the compounds of formula I in medical field, particularly in the preparation of medicaments for treating and preventing diabetes (in particular type II diabetes), hyperglycemia, X syndrome, hyperinsulinemia, obesity, atherosclerosis and all kinds of diseases modulated by immune system.

BACKGROUND ART

Dipeptidyl peptidase IV (DPP-IV) is a multifunctional type II transmembrane glycosylated protein that is widely expressed in the tissues of various mammals, which is a type of T cell activation antigen CD26 and is also a type of adenosine deaminase (ADA) binding protein. The single chain of the human DPP-IV (hDPP-IV) consists of 766 amino acids, which are divided into 5 structural domains: cytomere domain (1-6), transmembrane domain (7-28), highly glycosylated domain (29-323), cysteine-rich domain (324-551) and catalytic domain (552-766), and different species slightly differ from each other in terms of the lengths of these domains. Soluble DPP-IV is a homodimer of about 210-290 kDa and can also polymerize to form a complex of up to 900 kDa. DPP-IV binds with membrane via a hydrophobic helix formed by highly glycosylated domain and cysteine-rich domain at amino-terminal, and its serine protease domain at carboxyl-terminal is homologous to $\alpha/\delta$ hydrolase. The dimer form of DPP-IV is a precondition that it takes effect (heterodimer is a type of fibroblast activated protein FAP$\alpha$).

It is generally agreed that DPP-IV plays an important role in neuropeptide metabolism, T cell activation, cancer cell and endothelial attachment and entry of HIV into lymphocyte. DPP-IV can specifically cleave a dipeptide from N-terminal of a peptide in which the amino acid next to the last is mainly proline, alanine or hydroxyproline. The substrate by which DPP-IV takes effect includes two types of incretins that play an important role in the course of $T_2DM$ immune response signal transduction: segment of glucagon-like peptide 1 ($GLP-1_{7-36}$) and gastric inhibitory peptide ($GIP_{1-42}$). GLP-1 and GIP are incretins that are respectively secreted by gastric mucosa L cells and K cells in response to carbohydrates and fats taken in, and play an important role in stabilizing postprandial blood sugar concentration. After dining, gastric mucosa stress-secretes GLP-1 and GIP, both of which act on pancreas to strengthen glucose-induced insulin secretion, and modulate blood sugar concentration. Whereas, DPP-IV in vivo may hydrolyze them to generate the corresponding amino-terminal amputated $GIP_{3-42}$ and $GLP-1_{9-36}$, so that they will lose their insulin-inducing activity. Thus it can be seen, an inhibitor of DPP-IV is capable of strengthening the activity of GIP and GLP-1, and correspondingly improving the sugar tolerance level.

The DPP-IV deficient mouse experimental results obtained by Marguet et al and Conarello et al demonstrated that DPP-IV deficient mouse could completely survive and possessed normal phenotype; meanwhile, as compared with wild-type mouse, DPP-IV deficient mouse also exhibited a higher sugar tolerance and a higher blood insulin, GLP-1 concentration.

To sum up, inhibiting plasma DPP-IV activity is effective for reducing blood sugar concentration, which acts in at least three mechanisms listed below: firstly, to protect the activity of insulin: under physiological condition, the half life of intact GLP-1 in circulating blood is less than 1 min, and inactive metabolite of GLP-1 after degradation with DPP-IV can bind with GLP-1 receptor to antagonize active GLP-1, to thereby shorten the actuation duration of GLP-1 that is injected alone, while an inhibitor of DPP-IV can completely protect endogenous and even exogenous GLP-1 from deactivation by DPP-IV. It is known that GLP-1 has various physiological activities, including promoting expression of insulin gene, promoting growth of $\beta$ cells, inhibiting secretion of glucagons, gaining a full abdomen feeling, reducing ingestion, and inhibiting gastric emptying, to thereby normalize the blood sugar level; and an inhibitor of DPP-IV can reduce the antagonistic action of GLP-1 metabolite in addition to increasing the level of GLP-1. Besides, GIP secreted by k cells at upper part of small intestine, by acting on G protein-coupled receptor, increase the activity of adenyl cyclase, activate enzyme A2. to increase calcium ion level in cells, and promote release of insulin. GIP can also promote transcription and translation of proinsulin gene, up-regulate glucose transfer of plasma membrane and increase activity of $\beta$ cell hexokinase, thus GIP is effective for treating type II diabetes ($T_2DM$). However, being similar to GLP-1, endogenous GIP is also rapidly deactivated by DPP-IV. Deacon et al revealed that, after intravenous injection of GIP to a pig, the immunocompetence of intact GIP shown by radioimmunoassay was only 14.5%. When an inhibitor of DPP-IV was used, the immunocompetence of GIP was increased to 49%. This demonstrated that although DPP-IV is not the unique enzyme that degrades GIP in vivo, it plays an important role in the deactivation of GIP. Clearly, an inhibitor of DPP-IV can protect active incretin so that the later can take its effect.

Secondly, to stimulate the regeneration of islet $\beta$ cells: Pospisilik et al administered P32/98 (an inhibitor of DPP-IV) to a streptozotocin-induced DM male mouse, 2 times/d; after 7 weeks, it was observed by immunohistochemical analysis that, as compared with the control group, the number of islets was increased by 35%, the number of overall $\beta$ cells was increased by 120%, the fraction of islet $\beta$ cells was increased by 12%, and the plasma insulin level was approaching to normal. The effect of an inhibitor of DPP-IV for stimulating the regeneration of insulin and increasing the survival of $\beta$ cells may be due to that it improves the binding between GLP-1 and GLP-1 receptor on the surface of nestin-positive islet-derived progenitor (NIP) cells in islets, which thereby promotes the NIP cells to differentiate into islet cells.

Thirdly, to improve sugar tolerance and insulin sensitivity: it was shown by study that an inhibitor of DPP-IV was not only effective for treating DM, but also could take a preventive effect in terms of postponing the occurrence and development of DM. Sudre et al studied the treatment of obese mouse by using FE 999011 (a long-acting inhibitor of DPP-IV), and proved that FE 999011 slowed down the release of glucose in a dose-dependent manner, and the application of FE 999011, 10 mg/kg, 2 times/d, could increase the sugar tolerance. A long-term treatment by using the same dose as above-mentioned could postpone the occurrence of hyperglycemia in obese mouse by 21 d, and meanwhile could enhance the symptoms such as polydipsia and polyphagia, reduce the occurrence of hypertriglyceridemia, and prevent increasing of free fatty acids in blood; moreover, after the treatment, the basic plasma GLP-1 level was increased, and the pancreatic GLP-1 receptor gene expression was obviously up-regulated. Thus, the researchers considered that an inhibitor of DPP-IV could postpone the development of impaired glucose tolerance into type II diabetes. It was also suggested in other studies that the application of an inhibitor of DPP-IV could improve impaired glucose tolerance, increase insulin sensitivity, and improve the response of β cells to glucose.

Thus, an inhibitor of DPP-IV is capable of treating type II diabetes and other diseases modulated by DPP-IV.

CONTENTS OF THE INVENTION

The object of the present invention is to provide a type of inhibitors of dipeptidyl peptidase IV (DPP-IV) having novel structures, which, by inhibiting the activity of dipeptidyl peptidase IV, protect enteroinsulin from degradation, improve impaired glucose tolerance and increase insulin sensitivity, to fulfill the purpose of reducing blood sugar level, and thus are capable of effectively treating diabetes and other diseases modulated by DPP-IV.

The present invention provides novel compounds of formula I as defined in the claims, or the possible isomers, the pharmaceutically acceptable salts, the solvates, the hydrates or the prodrugs thereof,

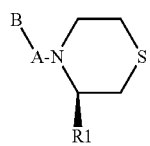

Formula I wherein:

R1 is selected from hydrogen, cyano, halogen or trifluoromethyl;

A is an amino acid, which amino acid contains at least one functional group at its side chain;

B is a compound covalently attached to the functional group at the side chain of A, and is selected from polypeptides consisting of 0 to 5 amino acids.

In one embodiment of the present invention, A in the formula I is α-amino acid.

In another embodiment of the present invention, A in the formula I is natural α-amino acid.

In another embodiment of the present invention, A in the formula I is unnatural amino acid.

In another embodiment of the present invention, A in the formula I is selected from the group consisting of leucine, valine, glycine, alanine, valine, isoleucine, phenylalanine, proline, tryptophan, serine, tyrosine and cysteine, preferably valine.

The most preferred compounds of the present invention are:

Compound 1: (R)-3-cyano-4-(2-amino-3-methyl-butyryl)thiomorpholine hydrochloride; or Compound 2: (R)-3-cyano-4-(2-amino-4-methyl-pentanoyl)thiomorpholine hydrochloride;

or the possible isomers, the pharmaceutically acceptable salts, the solvates, the hydrates or the prodrugs thereof.

In another aspect, the present invention relates to a method for preparing the compounds of formula I or the pharmaceutically acceptable salts or hydrates thereof.

The compounds of formula I herein may be prepared by reacting BOC-protected A with thiomorpholine-(R)-3-carboxylic acid amide according to the following equation:

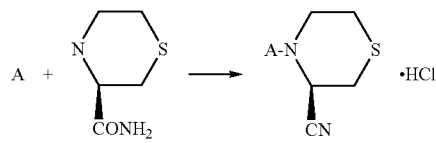

wherein, A is an amino acid, which amino acid contains at least one functional group at its side chain, preferably valine and leucine.

Concretely, amino acid, as protected with BOC, and thiomorpholine-(R)-3-carboxylic acid amide in equal mole are dissolved in dry THF, then 1.5 folds of EDCI and 1.5 folds of HOBT are added, and 2 folds of diisopropylethylamine is further added dropwise, followed by stirring at room temperature for 12 h-16 h. After completion of the reaction, the reaction product is concentrated under reduced pressure, and diluted by adding water, and then extracted with ethyl acetate. The obtained organic phase is dried with anhydrous sodium sulfate for 4 h, from which the solvent is removed under reduced pressure, and then the residue is dissolved in dry THF, to which is added 2 folds of trifluoroacetic anhydride. After stirring for 1 h, the product is washed with saturated NaHCO$_3$ until no air bubble occurs, and is then extracted with ethyl acetate, dried with anhydrous sodium sulfate for 4 h, and separated with silica gel chromatographic column (ethyl acetate:cyclohexane=1:4), obtaining a colorless oily substance. The oily substance is dissolved in 3N ethyl acetate hydrochloride, followed by stirring for 5 h, obtaining the target compound. If necessary, the compound of formula I may be further converted into pharmaceutically acceptable salts, solvates, hydrates or the prodrugs thereof according to conventional methods in the art.

In another aspect, the present invention relates to a method for preparing a compound of formula III, which is a key intermediate for preparing the compound of formula I. The present invention provides a new kind of stereoselective cyclization process, that is simple and easy to operate, and is suitable for large-scale synthesis, for the preparation of a stereoselective compound of formula III. The compound of formula III may be converted by ammonification into a compound of formula II, and the compound of formula II may further react with A, obtaining the compound of formula I.

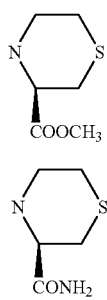

Formula III

Formula II

The compound of formula III of the invention may be prepared according to the following reaction pathway:

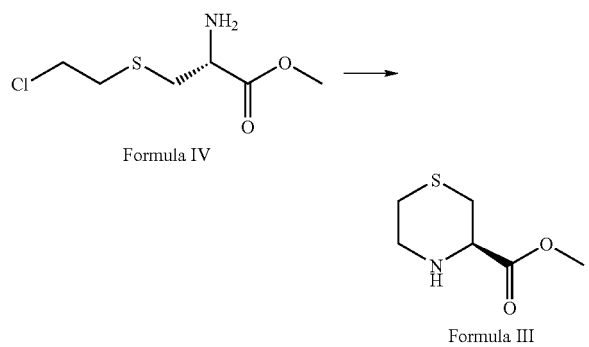

Formula IV

Formula III

Concretely, a compound of formula IV undergoes stereoselective cyclization reaction in water in the presence of a base as an acid-binding agent, obtaining the compound of formula III. The base as an acid-binding agent includes, but is not limited to, sodium hydroxide, potassium hydroxide, triethylamine, sodium bicarbonate, sodium carbonate, and etc., preferably sodium bicarbonate.

Please see Example 1 for the concrete preparation procedures of the compound of formula III thiomorpholine-3-carboxylic acid methyl ester hydrochloride.

The present invention further relates to a pharmaceutical composition comprising a compound of formula I or the possible isomers, the pharmaceutically acceptable salts, the solvates, the hydrates or the prodrugs thereof, and one or more pharmaceutically acceptable vehicles or excipients.

The term "pharmaceutical composition" herein refers to any product that is formed by mixing one or more active ingredients with one or more inert ingredients which form the vehicles, or by direct or indirect combination, complexation or aggregation of any two or more of these ingredients, or by decomposition of one or more of these ingredients, or by other type of reaction or interaction of one or more of these ingredients. Thus, the pharmaceutical composition herein includes any compositions formed by mixing the compound of the present invention with pharmaceutically acceptable vehicles.

The pharmaceutical composition herein may further comprise one or more of other active ingredients, for example, one or more of other inhibitors of DPP-IV. The other active ingredient is selected from insulin sensitizers, PPAR agonists, biguanides or PTP-1B inhibitors, and etc.

In another aspect, the present invention relates to use of a compound of formula I or the possible isomers, the pharmaceutically acceptable salts, the solvates, the hydrates or the prodrugs thereof for the preparation of a medicament for treating diseases associated with dipeptidyl peptidase IV, wherein the diseases associated with dipeptidyl peptidase IV include, but are not limited to, diabetes (in particular type II diabetes), hyperglycemia, X syndrome, hyperinsulinemia, obesity, atherosclerosis and all kinds of diseases modulated by immune system.

In another aspect, the present invention relates to a method for treating diseases associated with dipeptidyl peptidase IV, which comprises administering to a patient in need of the treatment a therapeutically effective amount of the compound of formula I or the possible isomers, the pharmaceutically acceptable salts, the solvates, the hydrates or the prodrugs thereof, wherein the diseases associated with dipeptidyl peptidase IV include, but are not limited to, diabetes (in particular type II diabetes), hyperglycemia, X syndrome, hyperinsulinemia, obesity, atherosclerosis and all kinds of diseases modulated by immune system.

Mode of Carrying out the Invention

The following examples are preferred embodiments of the present invention, and serve to illustrate the present invention, and shall not be understood to limit the present invention in any manner.

The melting point of the compound was determined by using RY-1 melting point apparatus, the thermometer being not calibrated. Mass spectrum was determined by using Micromass ZabSpec high resolution mass spectrograph. $^1$H NMR was determined by using JNM-ECA-400 superconductive NMR spectrometer, the working frequency of $^1$H NMR being 400 MHz.

EXAMPLE 1

Preparation of thiomorpholine-(R)-3-carboxylic acid amide

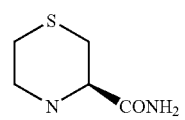

Step 1. Preparation of 2-hydroxyethyl cysteine 109.5 g (0.9 mol) L-cysteine was placed in a 2000 ml flask, and dissolved with 1000 ml water, to which was added 24 ml of 1 mol/l NaOH solution. In an ice bath, 96 ml (1.8 mol) ethylene oxide was slowly added dropwise into the cysteine solution. After stirring 1 h, the ice bath was removed and the mixture was warmed to room temperature and further reacted for 1 h. The reaction product was extracted with 1000 ml anhydrous ethyl ether for four times, while collecting the aqueous layers. The aqueous layers were evaporated to dryness obtaining a yellow crystal product. The yellow crystal product was recrystallized with water:ethanol=85 ml:350 ml, filtered, washed with 2000 ml of 95% ethanol, and dried obtaining 121.8 g of a white crystal product, yield 74.3%.

$^1$H-NMR (400 MHz, $D_2O$) δ: 2.80 (t, 2H, J=6.036 Hz), 3.08 (dd, 1H, $J_1$=7.48 Hz, $J_2$=14.80 Hz), 3.18 (dd, 1H, $J_1$=4.27 Hz, $J_2$=14.81 Hz), 3.77-3.81 (m, 2H), 3.96 (dd, 1H, $J_1$=4.272 Hz, $J_2$=7.816 Hz).

Step 2. Preparation of 2-chloroethyl cysteine 40 g (0.24 mol) 2-hydroxyethyl cysteine was placed in a 1000 ml flask, to which was added 550 ml concentrated hydrochloric acid, followed by reflux for 7 h. After completion of the reflux, the reaction mixture was allowed to stand at room temperature to separate out white crystal, which was filtered and dried obtaining 41.6 g of a white crystal product, yield 93.8%.

$^1$H-NMR (400 MHz, D$_2$O) δ: 3.01-3.04 (m, 2H), 3.12 (dd, 1H, J$_1$=7.35 Hz, J$_2$=15.07 Hz), 3.26 (dd, 1H, J$_1$=4.444 Hz, J$_2$=14.984 Hz), 3.78-3.84 (m, 2H), 4.27-4.30 (m, 1H).

Step 3. Preparation of methyl 2-chloroethyl cysteine hydrochloride 39 g (0.21 mol) 2-chloroethyl cysteine was dissolved with 500 ml anhydrous methanol, and cooled with an ice bath. 80 ml (1.1 mol) thionyl chloride was slowly added dropwise to the solution in the ice bath. Thereafter, the reaction mixture was warmed and reacted at room temperature for 24 hours. After removing the solvent under reduced pressure, the reaction product was dissolved with anhydrous methanol (200 ml×2) and then evaporated to dryness, to remove redundant thionyl chloride. The obtained solid was recrystallized with 50 ml anhydrous methanol and 160 ml anhydrous ethyl ether, resulting in 37.5 g of a white crystal, yield 76.1%.

$^1$H-NMR (400 MHz, D$_2$O) δ: 2.99-3.049 (m, 2H), 3.20 (dd, 1H, J$_1$=7.50 Hz, J$_2$=14.00 Hz), 3.34 (dd, 1H, J$_1$=4.480 Hz, J$_2$=15.034 Hz), 3.78-3.82 (m, 2H), 3.90 (s, 3H), 4.45 (dd, 1H, J$_1$=4.50 Hz, J$_2$=7.48 Hz).

Step 4. Preparation of thiomorpholine-3-carboxylic acid methyl ester hydrochloride 20 g (0.085 mol) methyl 2-chloroethyl cysteine hydrochloride was dissolved with 200 ml water, and a solution of 7.2 g (0.085 mol) sodium bicarbonate dissolved in 120 ml water was added dropwise to the above-obtained solution under ice bath condition, and then the mixed solution was allowed to react by keeping a constant temperature in the bath ice for 1 hour. The obtained reaction product was extracted with ethyl acetate (100 ml×3), and the resulting ester layers were combined, and dried with anhydrous sodium sulfate for 4 hours. The solvent was removed by evaporation under reduced pressure. The resulting residue was dissolved with 400 ml anhydrous methanol, and reacted with stirring at room temperature for 5 days, followed by removing solvent by evaporation under reduced pressure. The resulting residue was recrystallized with anhydrous methanol/ethyl acetate, obtaining 8.9 g of a white crystal, yield 49.2%.

$^1$H-NMR (400 MHz, DMSO-d$_6$) δ: 2.86-2.88 (m, 1H), 2.96-2.99 (m, 1H), 3.06-3.22 (m, 3H), 3.48-3.50 (m, 1H), 3.78 (s, 3H), 4.42 (dd, 1H, J$_1$=3.52 Hz, J$_2$=8.56 Hz), 10.1 (brs, 2H).

Step 5. Preparation of thiomorpholine-(R)-3-carboxylic acid amide 8.9 g (0.042 mol) thiomorpholine-3-carboxylic acid methyl ester hydrochloride was dissolved with 200 ml anhydrous methanol and NH$_3$ was charged. The reaction mixture was allowed to react for 48 hours, and then the solvent was evaporated to dryness. The resulting residue was dissolved with anhydrous ethanol and filtered to remove insoluble matter, and then the solvent was evaporated to dryness. Thereafter, the resulting residue was recrystallized with anhydrous methanol/anhydrous ethyl ether, obtaining 5.44 g of a white crystal, yield 89.2%.

$^1$H-NMR (400 MHz, CDCl$_3$) δ: $^1$H-NMR (400 MHz, CDCl$_3$) δ ppm: 2.45-2.47 (d, 1H, J=8.4 Hz), 2.50-2.55 (m, 2H), 2.56-2.58 (m, 1H), 3.21-3.28 (m, 2H), 5.33 (s, 1H), 7.08 (s, 1H), 7.26 (s, 1H).

EXAMPLE 2

Preparation of Compound 1

(R)-3-cyano-4-(2-amino-3-methyl-butyryl)thiomorpholine hydrochloride

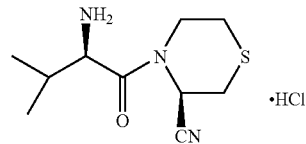

0.217 g (0.001 mol) Boc-Val and 0.147 g (0.001 mol) thiomorpholine-(R)-3-carboxylic acid amide prepared in Example 1 were dissolved with 20 ml dry THF, to which was added 0.29 g (0.0015 mol) EDCI and 0.18 g HOBT (0.0015 mol), and was further added dropwise 0.35 ml (0.002 mol) diisopropylethylamine, followed by stirring at room temperature for 12 h. After completion of the reaction, the reaction product was concentrated under reduced pressure. The residue was diluted with 20 ml water and extracted with ethyl acetate (50 ml×3). The obtained organic phase was dried with anhydrous sodium sulfate for 4 h, followed by removing the solvent under a reduced pressure. The resulting residue was dissolved with 20 ml dry THF, to which was added 2.8 ml (0.002 mol) trifluoroacetic anhydride, followed by stirring for 1 h. The obtained product was washed with a saturated aqueous solution of NaHCO$_3$ until no air bubble occurred, and then extracted with ethyl acetate (50 ml×3), dried with anhydrous sodium sulfate for 4 h, and separated with a silica gel chromatographic column (AcOEt:cyclohexane=1:4), obtaining a colorless oily substance. The oily substance was dissolved with 30 ml 3N ethyl acetate hydrochloride, followed by stirring for 5 h, resulting in a white precipitate. The precipitate was filtered, and then the obtained filter cake was washed with ethyl acetate, resulting in 0.072 g of the target compound as a white solid, yield 27.2%.

$^1$H-NMR (400 MHz, DMSO) δ ppm: 0.90-0.95 (m, 6H), 2.01-2.06 (m, 1H), 2.50 (s, 1H), 2.85-3.01 (m, 3H), 3.39-3.44 (m, 1H), 4.33-4.44 (m, 2H), 6.15 (s, 1H), 8.43 (brs, 3H).

FAB-MS m/e: 228 [M+1]$^+$.

EXAMPLE 3

Preparation of Compound 2

(R)-3-cyano-4-(2-amino-4-methyl-pentanoyethiomorpholine hydrochloride

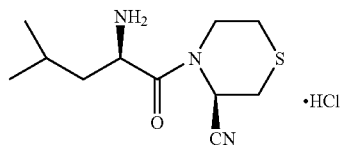

0.231 g (0.001 mol) Boc-Leu and 0.147 g (0.001 mol) thiomorpholine-(R)-3-carboxylic acid amide prepared in Example 1 were dissolved with 20 ml dry THF, to which was added 0.29 g (0.0015 mol) EDCI and 0.18 g HOBT (0.015 mol), and was further added dropwise 0.35 ml (0.002 mol) diisopropylethylamine, followed by stirring at room temperature for 12 h. After completion of the reaction, the reaction product was concentrated under reduced pressure. The residue was diluted with 20 ml water and extracted with ethyl acetate (50 ml×3). The obtained organic phase was dried with anhydrous sodium sulfate for 4 h, followed by removing the solvent under a reduced pressure. The resulting residue was dissolved with 20 ml dry THF, to which was added 2.8 ml (0.002 mol) trifluoroacetic anhydride, followed by stirring for 1 h. The obtained product was washed with a saturated aqueous solution of $NaHCO_3$ until no air bubble occurred, and then extracted with ethyl acetate (50 ml×3), dried with anhydrous sodium sulfate for 4 h, and separated with a silica gel chromatographic column (ethyl acetate:cyclohexane=1:4), obtaining a colorless oily substance. The oily substance was dissolved with 30 ml 3N ethyl acetate hydrochloride, followed by stirring for 5 h, resulting in a white precipitate. The precipitate was filtered, and then the obtained filter cake was washed with ethyl acetate, resulting in 0.096 of the target compound as a white solid, yield 34.8%.

$^1$H-NMR (400 MHz, $D_2O$) δ ppm: 0.77-0.81 (m, 6H), 1.41-1.61 (m, 1H), 2.48-2.52 (d, 1H, J=7.6 Hz), 2.68-2.28 (m, 2H), 2.90-2.95 (m, 1H), 3.51-3.57 (t, 2H, J=12.4 Hz), 3.88-3.93 (d, 1H, J=14.4 Hz), 3.35-3.70 (m, 1H), 5.97 (s, 1H).

EI-MS m/e: 241 [M$^+$].

EXAMPLE 4

Determination of DPP-IV Inhibitory Activity and IC$_{50}$ of Compounds 1 and 2

Step 1. Preparation of DPP-IV

Cultivation of human colon carcinoma cell-line cells (Caco-2): Caco-2 cells were cultivated in a culture medium of DMEM (high glucose, containing 10% fetal bovine serum, 1% NAA), and the cell lines were passaged in a proportion of 1:1 or 1:2; after nearly reaching confluence, the cells were further cultivated for 2-3 weeks, while changing the medium once every 2-3 days. When the cells were observed to exhibit brush border projections, it demonstrated that the cells had been differentiated, then the cells were collected.

Preparation of DPP-IV: the cells were washed with a pre-cooled PBS for 2-3 times, and 0.5-1 ml ice-cold 10 mM Tris-HCl (containing 0.15 M NaCl, 0.04 t.i.u aprotinin, 0.5% nonionic detergent P40, pH 8) was added to each culture bottle to lysate the cells, followed by collecting them in a centrifuge tube. After centrifugation at 4° C., 35000 g for 30 mM, the obtained supernatant was collected, and subjected to a protein content detection, and then stored in a low temperature refrigerator.

Step 2. Determination of Activity of DPP-IV and Screening of Compounds

The test groups included enzyme control group, substrate control group, enzyme reaction control group, and compound group, and the test was carried out in a 96-pore plate, using 150 μL reaction system. In the 96-pore plate, a diluted test compound was added in the compound group, 30 μL/pore; 20 μL DPP-IV solution was added in the enzyme control group, as well as in the compound group; an analytic buffer (25 mM Tris-HCl pH 7.4, containing 140 mM NaCl, 10 mM KCl, 1% bovine serum albumin) was added in 130 μL to the enzyme control group, in 125 μL to the substrate control group, in 105 μL to the enzyme reaction control group, and in 75 μL to the compound group; and then 25 μL substrate (1 mM) was added, followed by reacting at room temperature for 10 min. No substrate was added in the enzyme control group. After reacting for 10 min, 25% glacial acetic acid was added in 19 μL/pore to terminate the reaction. The absorbance was determined by using an enzyme calibrating apparatus at a wavelength of 405 nM. The inhibitory rates as calculated were listed in the following table.

| No. of compound | Concentration (nM) | Inhibitory rate(%) | IC$_{50}$ |
|---|---|---|---|
| Compound 1 | 10 | 7.65 ± 0.68 | 188.7 ± 26.4 |
| | 30 | 13.15 ± 1.92 | |
| | 100 | 40.27 ± 3.09 | |
| | 300 | 73.02 ± 1.74 | |
| | 1000 | 101.01 ± 1.36 | |
| Compound 2 | 100 | 24.07 ± 2.41 | |
| | 300 | 47.16 ± 0.64 | |

The invention claimed is:

1. A compound of formula I, or the possible isomers or pharmaceutically acceptable salts thereof,

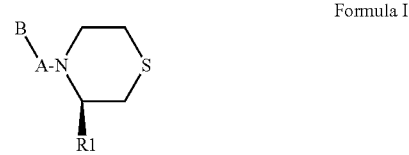

Formula I wherein:
R1 is cyano;
A is a natural α-amino acid, which amino acid contains at least one functional group at its side chain; and
B is absent.

2. The compound according to claim 1, wherein A in the formula I is selected from the group consisting of leucine, valine, alanine, isoleucine, phenylalanine, proline, tryptophan, serine, tyrosine and cysteine.

3. The compound according to claim 1 selected from:
(R)-3-cyano-4-(2-amino-3-methyl-butyryl)thiomorpholine hydrochloride;
(R)-3-cyano-4-(2-amino-4-methyl-pentanoyl)thiomorpholine hydrochloride; or
the possible isomers or pharmaceutically acceptable salts thereof.

4. A method for preparing the compound according to claim 1 comprising reacting BOC-protected A with thiomorpholine-(R)-3-carboxylic acid amide according to the following equation:

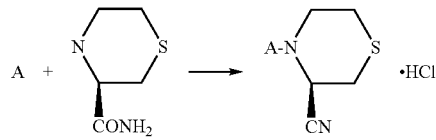

wherein A is a natural α-amino acid, which amino acid contains at least one functional group at its side chain.

5. The method according to claim 4, wherein the key intermediate thiomorpholine-(R)-3-carboxylic acid amide in the method is prepared by the steps of: subjecting a compound of formula IV to stereoselective cyclization reaction in water in the presence of a base as an acid-binding agent, obtaining a compound of formula III,

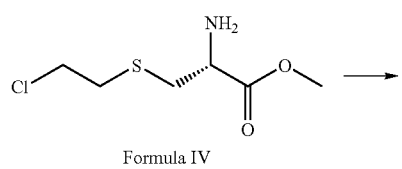

Formula IV

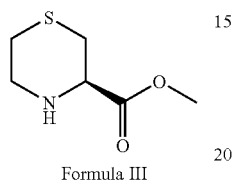

Formula III and then converting by ammonification the compound of formula III into thiomorpholine-(R)-3-carboxylic acid amide.

6. A pharmaceutical composition comprising a compound of formula I according to claim 1 or the possible isomers or pharmaceutically acceptable salts thereof, and one or more pharmaceutically acceptable vehicles or excipients.

7. A method for treating diseases associated with dipeptidyl peptidase IV, wherein the diseases associated with dipeptidyl peptidase IV are selected from type II diabetes, hyperglycemia, X syndrome, hyperinsulinemia, obesity and atherosclerosis which comprises the step of administering to a patient in need of the treatment a therapeutically effective amount of the compound of formula I according to claim 1 or the possible isomers, the pharmaceutically acceptable salts thereof.

8. The compound according to claim 1, wherein A in the formula I is valine.

9. A compound of formula I, or the possible isomers or pharmaceutically acceptable salts thereof,

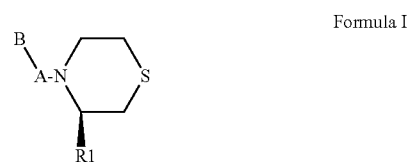

Formula I wherein:
R1 is cyano;
A is valine, which valine contains at least one functional group at its side chain; and
B is absent.

10. The method of claim 7, wherein the diabetes is type II diabetes.

* * * * *